(12) United States Patent
Toda et al.

(10) Patent No.: US 7,314,732 B2
(45) Date of Patent: *Jan. 1, 2008

(54) DRUG AND MANUFACTURING METHOD OF SAME

(75) Inventors: Nobuhiro Toda, Kobe (JP); Sachio Yoshimoto, Nishinomiya (JP); Yukizo Kudo, Akita (JP)

(73) Assignee: TFK Inc., Hyogo (JP)

( * ) Notice: Subject to any disclaimer, the term of this patent is extended or adjusted under 35 U.S.C. 154(b) by 344 days.

This patent is subject to a terminal disclaimer.

(21) Appl. No.: 10/784,209

(22) Filed: Feb. 24, 2004

(65) Prior Publication Data

US 2004/0166093 A1    Aug. 26, 2004

Related U.S. Application Data

(63) Continuation-in-part of application No. 09/958,928, filed as application No. PCT/JP01/01100 on Feb. 15, 2001, now Pat. No. 6,797,279.

(30) Foreign Application Priority Data

Feb. 17, 2000  (JP) .............................. 2000-40218

(51) Int. Cl.
   *C12N 1/12* (2006.01)
   *C12N 1/20* (2006.01)
   *C12P 1/00* (2006.01)
   *C12P 1/04* (2006.01)

(52) U.S. Cl. ..................... 435/41; 435/170; 435/252.1; 435/822

(58) Field of Classification Search ...................... None
See application file for complete search history.

(56) References Cited

U.S. PATENT DOCUMENTS

| | | | |
|---|---|---|---|
| 2,771,480 A * | 11/1956 | Chasanov et al. | 554/182 |
| 4,467,035 A | 8/1984 | Harasawa et al. | |
| 5,115,084 A * | 5/1992 | Himmelblau | 528/230 |
| 5,158,939 A | 10/1992 | Takayama et al. | |
| 5,648,264 A * | 7/1997 | Kume | 435/264 |
| 5,935,808 A | 8/1999 | Hirschberg et al. | |
| 5,955,321 A * | 9/1999 | Bijl | 435/86 |
| 6,180,099 B1 | 1/2001 | Paul | |
| 6,797,279 B2 * | 9/2004 | Toda et al. | 424/439 |
| 2004/0166093 A1 * | 8/2004 | Toda et al. | 424/93.4 |

FOREIGN PATENT DOCUMENTS

| | | |
|---|---|---|
| EP | 01 90 4487 | 5/2005 |
| JP | 47-025379 | 10/1972 |
| JP | 53-019673 | 2/1978 |
| JP | 60-036446 | 2/1985 |
| JP | 04-248982 | 9/1992 |
| JP | 07-082556 | 3/1995 |

OTHER PUBLICATIONS

The above reference is cited in the Office Action mailed Jan. 16, 2004, by the Korean Patent Office for the Korean Patent Application No. 10-2001-70131118 corresponding to the above-identified application (English Translation).

Huang Zebo. et al. "Studies on Polysaccharides From Three Edible Species of *Nostoc* (Cyanobacteria) With Different Colony Morphologies: Comparison of Monosaccharide Compositions and Viscosities of Polysaccharides From Field Colonies and Suspension Cultures"; 1998; vol. 34, No. 6; pp. 962-968.

Watanabe Masanori et al.; Flocculating Property of Extracellular Polymeric Substance Derived From a Marine Photosynthetic Bacterium, *Rhodovulum* sp; May 1999; vol. 87, No. 5; pp. 625-629.

* cited by examiner

*Primary Examiner*—David M. Naff
*Assistant Examiner*—Deborah K. Ware
(74) *Attorney, Agent, or Firm*—Nixon & Vanderhye P.C.

(57) ABSTRACT

The drug of the present invention, and a method of manufacturing the drug are so arranged that a photosynthetic bacterium is incubated together with a lactic acid bacterium so as to cause the photosynthetic bacterium to produce a viscous material in a liquid medium, the photosynthetic bacterium being *Rhodopseudomonas capsulatas* FERMBP-7434 strain, and the lactic acid bacterium being *Lactobacillus* spp., and then a metabolic product, which is to be contained in the drug, is separated from the liquid medium. Health can be recovered by using the drug in such a small quality that is not hard on a user.

11 Claims, 1 Drawing Sheet

DRUG AND MANUFACTURING METHOD OF SAME

This application is a Continuous-in-part (CIP) application of a parent U.S. patent application Ser. No. 09/958,928 filed in the United States on Jan. 3, 2002 now U.S. Pat. No. 6,797,279, which is the National Phase of an international PCT application No. PCT/JP01/01100, filed on Feb. 15, 2001, which claims priority under 35 U.S.C. § 119(a) on Japanese Patent Application No. 2000-040218 filed on Feb. 17, 2000, the entire contents of all of which are hereby incorporated by reference.

FIELD OF THE INVENTION

The present invention relates to a drug using a red (purple) photosynthetic bacterium that is useful for maintaining and recovering health, and a manufacturing method the same.

BACKGROUND OF THE INVENTION

Conventionally, Japanese Un-examined Patent Application, Tokukaisho No. 47-25379 (published on Oct. 20, 1972) discloses that red photosynthetic bacteria can be utilized for sewage treatment. The red photosynthetic bacteria are red non-sulfur bacterium (Athiorhodaceae) and red sulfur bacterium (Thiorhodaceae).

However, the prior art does not disclose or teach that ingestion of the red photosynthetic bacteria is effective for recovering health.

The inventors of the present invention conducted an intensive studies on the red photosynthetic bacteria incubated in a various methods. As a result, the inventors of the present invention found out that a metabolic product produced by the red photosynthetic bacteria incubated in a specific incubation method is effective for recovering heath, thereby accomplishing the present invention.

SUMMARY OF THE INVENTION

The present invention has an object of providing a drug effective for maintaining and recovering health, and a manufacturing method thereof, the drug and the manufacturing thereof using a red photosynthetic bacterium.

In order to attain the foregoing object, a drug of the present invention is so arranged as to contain a metabolic product prepared by incubating a photosynthetic bacterium together with a lactic acid bacterium so as to cause the photosynthetic bacterium to produce a viscous material, the photosynthetic bacterium being *Rhodopseudomonas capsulatas* FERMBP-7434 strain.

In order to attain the foregoing object, a manufacturing method of the present invention for manufacturing a drug, includes the steps of: incubating a photosynthetic bacterium together with a lactic acid bacterium so as to cause the photosynthetic bacterium to produce a viscous material in a liquid medium, the photosynthetic bacterium being *Rhodopseudomonas capsulatas* FERMBP-7434 strain; and separating a metabolic product from the liquid medium.

Therefore, according to the arrangement and method, it is possible to stably producing a drug having an excellent function of recovering health, by containing a metabolic product by incubating *Rhodopseudomonas capsulatas* FERMBP-7434 strain together with a lactic acid bacterium so as to cause the photosynthetic bacterium to produce a viscous material.

For a fuller understanding of the nature and advantages of the invention, reference should be made to the ensuing detailed description taken in conjunction with the accompanying drawings.

DESCRIPTION OF THE EMBODIMENTS

Figure 1:
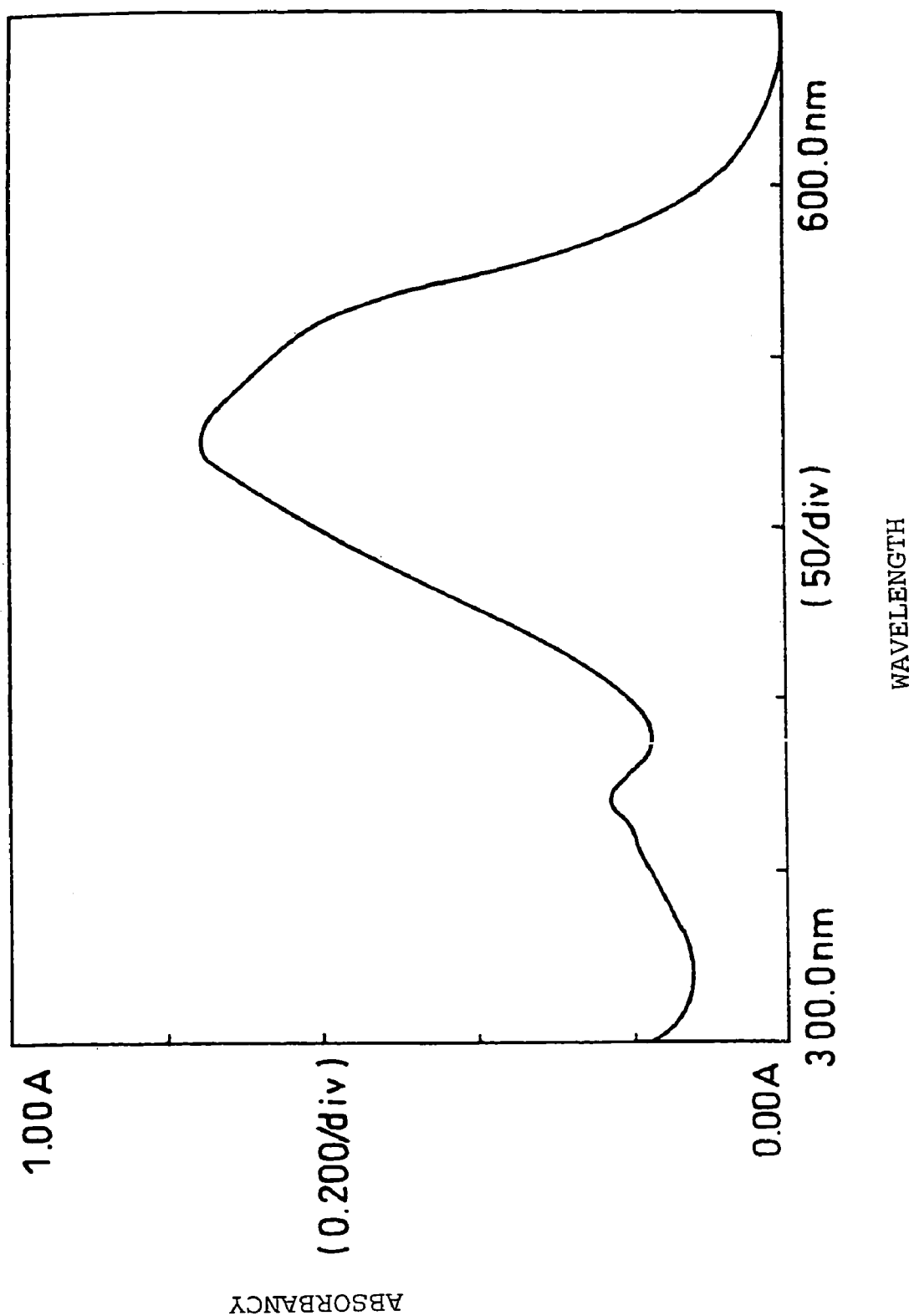
FIG. 1 is a graph illustrating absorption spectrum of an ether solution used for qualifying carotinoid materials in a sample 1 which is a dried biomass for a drug of the present invention.

Described below is an embodiment of the present invention.

A drug (TFK-RC) of the present invention contains a metabolic product of a photosynthetic bacterium that is obtained from a liquid medium prepared by incubating a bacterial solution including a photosynthetic bacterium and a lactic acid bacterium so as to produce in a large quantity a viscous material from the photosynthetic bacterium, the photosynthetic bacterium being *Rhodopseudomonas capsulatas* FERMBP-7434 strain.

The drug is prepared, for example, by using a concentrated biomass, the concentrated biomass diluted with water, the concentrated biomass dried, or the concentrated biomass freeze-dried. The concentrated biomass, which is a residue including each biomass having the metabolic product of the photosynthetic bacterium, is prepared, for example, by filtration of the liquid medium by means of centrifugation, and removing liquid from the filtrate.

The thus obtained drug, as explained later, was not toxic, and regular dosing (usage, intake, ingestion, applying on skin, etc.) of the drug showed no side effect. Moreover, observed was improvement of health condition of unhealthy people who had taken 30 mg to 450 mg, more preferably 120 mg to 300 mg of the drug per day for a period ranging from one week to 6 months for example, where the dosing was in one time or preferably divided into four times (morning, noon, night and before sleep). The dosing was carried out with consent of the unhealthy people and a medical doctor in charge for the unhealthy person. Note that dosages of the drag in the dosing are in dry weight.

The unhealthy people were suffering from, for example: cancer in the final stage, lymphogranuloma, severe diabetes, severe depression, severe cardiac disease, severe skin disease (including atopic dermatitis), impotency, epilepsy, hypertension (including low blood pressure), chronic constipation, chronic diarrhea, insomnia, menstrual pain, Alzheimer's disease, acute pneumonia, the autonomic imbalance, cerebral embolism, or polyp of the colon.

Because of this, it was deduced that the drug of the present invention improves autoimmune of the patients, and it was indicated that there was a possibility that the drug of the present invention had efficiency for recovering health condition of the unhealthy people who used it, even though system of its function was unknown. Moreover, it was indicated the drug was effective for maintaining the health of a health person who ingested it.

Table 1 shows cases of health recovery (cure) by the drug. Note that, in Table 1, ♥ is 90% or more, ♣ is 75% or more, ♦ is 50% or more, and ♠ is 10% or less. As to an ingestion amount per day, 60 mg to 120 mg of the drug was used in Case Group A, 90 mg to 210 mg of the drug was used in Case Group B, and 180 mg to 300 mg of the drug was used in Case Group C. Note that the periods of time or the days in the brackets in Table 1 are periods or time or days taken to fully recover or to almost-fully recover.

As clearly shown in Table 1, it was found that the concentrated biomass of the drug of the present invention is useful as a cosmetic (a hair growing drug, a hair tonic, a cosmetic material, a skin healing drug), and a quasi-drug (for example, a health drink). Especially, the concentrated biomass of the drug of the present invention has an antipruritic effect. By applying, on an insect bite, or itchy part of skin due to atopic dermatitis, an aqueous solution of the concentrated biomass in about 5% to 20% concentration, an antipruritic effect of the drug was observed. Thus, the drug is also useful as an antipruritic.

Further, when the concentrated biomass of the drug of the present invention was used in a so-called 24-hour bath, in which water is recycled by filtering off microorganisms and keeping a temperature of water therein for 24-hour usage, multiplication of a harmful coliform and legionella pneumophila was blocked. Thus, it was found that the drug of the present invention is also useful as a bath agent.

TABLE 1

| Case Group A | |
|---|---|
| ♥ Hangover | (1 to 3 hours) |
| ♥ Hemicrania | (1 to 24 hours) |
| ♥ Chronic Diarrhea | (30 to 90 days) |
| ♥ Split end of hair, Depilation | (30 to 90 days) |
| ♥ Pathological Grey Hair | (30 to 90 days) |
| ♥ Alopecia Areata | (30 to 90 days) |
| ♥ Insomnia | (30 to 90 days) |
| (Habitual users of a tranquilizer for more than 10 years) | |
| ♥ Menopausal Disorder | (30 to 120 days) |
| ♥ Chronic Constipation | (60 to 90 days) |
| ♥ Epilepsy | (60 to 120 days) |
| ♥ Common Cold | (3 to 48 hours) |
| ♥ Pollinosis | (14 to 90 days) |
| ♥ Chronic Fatigue | (30 to 90 days) |
| ♥ Menstrual Pain | (30 to 90 days) |
| ♥ Rough Dry Skin | (30 to 90 days) |
| ♥ Dermatitis | (30 to 90 days) |
| ♥ Gastrointestinal Infirmity | (30 to 120 days) |
| ♣ Muscle Stiffness of the Shoulder | (30 to 90 days) |
| ♣ Neuralgia | (30 to 120 days) |
| ♣ Low Back Pain | (60 to 120 days) |
| ♣ Arthritis | (60 to 120 days) |
| ♣ Chronic Alcoholism | (60 to 120 days) |
| CASE GROUP B | |
| ♥ Autonomic Imbalance | (30 to 90 days) |
| ♥ Acute Low Back Pain | (14 to 60 days) |
| ♥ Hypertension | (60 to 90 days) |
| ♥ Atopic Dermatitis | (60 to 120 days) |
| ♥ Depression | (60 to 120 days) |
| ♥ Myocardial Infarction | (60 to 120 days) |
| ♥ Polyp of the Colon | (90 to 180 days) |
| ♥ Acute Pneumonia | (7 to 14 days) |
| ♥ Gastric Ulcer | (60 to 90 days) |
| ♥ Autism | (60 to 120 days) |
| ♣ Gout | (60 to 120 days) |
| ♣ Brain Infarction | (60 to 120 days) |
| ♣ Senile Dementia | (60 to 120 days) |
| ♣ Rheumatism | (60 to 180 days) |
| ♣ Herniated Intervertebral Disk | (60 to 180 days) |
| ♣ Duodenal Ulcer | (60 to 90 days) |
| ♣ Cerebral Thrombosis | (90 to 120 days) |
| ♣ Senile Impotency | (60 to 180 days) |
| ♣ Diabetes Mellitus | (90 to 120 days) |
| ♦ Hepatitis C | (90 to 120 days) |
| ♦ Alzheimer's Disease | (90 to 120 days) |
| ♦ Bronchial Asthma | (90 to 120 days) |

TABLE 1-continued

| CASE GROUP C | |
|---|---|
| Cancers in the final stage (Remaining Days 2 to 6 months) | |
| ♥ Lung Cancer | (60 to 180 days) |
| ♥ Hepatoma (due to Hepatitis C) | (60 to 180 days) |
| ♥ Bone Tumor | (60 to 180 days) |
| ♥ Non-Hodgkin's Lymphoma | (60 to 180 days) |
| ♥ Brain Tumor | (60 to 180 days) |
| ♥ Prostate Cancer | (60 to 180 days) |
| ♣ Gastric Cancer | (60 to 180 days) |
| ♣ Colorectal Cancer | (60 to 180 days) |
| ♣ Multiple Myeloma | (60 to 180 days) |
| ♦ Leukemia | (90 to 180 days) |
| ♦ Pancreatic Cancer | (90 to 180 days) |
| ♣ Metastasis Ratio of the cancers | (three years) |
| ♣ Recurrence Ratio of the cancers | (three years) |

The photosynthetic bacterium is, for example, a red non-sulfur bacterium, which is a red photosynthetic bacterium, Athiorhodaceae Rhodopseudomonus, more preferably, *Rhodopseudomonas capsulatas*, or especially preferably *Rhodopseudomonas capsulatas* FERMBP-7434 strain that had been deposited at an international depository Authority for microorganisms.

The international depository authority is the Bioengineering industrial technology laboratory in the industrial technology general research institution of the department for Economy and Industry, whose address is 1-3, Higashi 1-chome, Tsukuba City, Ibaraki Prefecture, Japan (Post Code 305-8566). (Now, the Bioengineering industrial technology laboratory has been renamed as "AIST (National Institute of Advanced Industrial Science and Technology), whose address is AIST Tsukuba Central 6, 1-1-1 Higashi, Tsukuba City, Ibaraki Prefecture, Japan.)

The FERMBP-7434 strain was internationally deposited on Jan. 18, 2001, by requesting to transfer to depository under the terms of the Budapest Treaty, Bikokenyo No. P-17654, which had been domestically deposited at the international depository authority on Nov. 18, 1999 (original depository date). The name of the depositor is Biochem Industry Co., Ltd. (representative director: Toda). Address of the depositor is 2-25-D407, 1-chome, Wadayama-dori, Hyogo-ku, Kobe City, Hyogo Prefecture, Japan.

The lactic acid bacterium may be Lactobacillus spp. or Streptococcus spp., for example. The Lactobacillus spp. may be *Lactobacillus bulgalicus* and *Lactobacillus acidophilus*, for example. The Streptococcus spp. may be *Streptococcus lactis* and *Streptococcus thermophilus*, for example.

Explained below is incubation condition of the bacterial solution. To begin with, as the incubation condition, the bacteria and a liquid medium (pH 6.0 to pH 8.5) including organic materials, mainly low fatty acids (at least one of a saturated fatty acid and an unsaturated fatty acid), were poured into a transparent growth tank. The incubation was carried out in the growth tank with illumination of light at 3000 lux to 10000 lux, at a temperature ranging from 23° C. to 39° C., and under an anaerobic condition. The incubation reached a stationary phase in 72 hours at latest, so that the concentrated bacteria could be obtained from the liquid medium. The liquid medium contained biotin, thiamin, and niacin as growth factors.

The incubation condition is explained below with more details. To begin with, in a mixing tank for nutrition, prepared was a base medium made of a mixture of incubation substances $(NH_4)_2SO_4$, $KH_2PO_4$, $MgSO_4 \cdot 7H_2O$, NaCl, $NaHCO_3$, and yeast extract (including the above mentioned growth factors). In case of the incubation of the non-sulfur bacterium, low fatty acids such as acetic acid, propionic acid, and lactic acid, which were in a form of Na salt, were added into the base medium, so as to prepare the liquid medium (for example, at pH 7.0). Moreover, in case of the incubation of the red sulfur bacterium, $Na_2S.9H_2O$ was added into the base medium and adjusted by using KOH solution so as to prepare a liquid medium (at between pH 8.2 and 8.5).

Next, the liquid medium was transferred from the mixing tank for nutrition to a sealed and illuminated growth tank. Then, as the photosynthetic bacterium, for example, *Rhodopseudomonas capsulatas* FERMBP-7434 strain, which was a red non-sulfur bacterium (Athiorhodaceae), was inoculated into the sealed and illuminated growth tank.

Note that, the photosynthetic bacterium of this type also metabolizes starch, glucose, sucrose, alcohol, and other high molecular carbohydrates, thereby growing well, if various heterotrophic bacteria coexist, besides the organic acids that form the liquid medium. Because of this, it is more effective to inoculate, in the sealed and illuminated growth tank, various heterotrophic bacteria, such as the above-mentioned lactic acid bacteria, together with the photosynthetic bacterium, while adding those high molecular carbohydrates into the liquid medium.

In addition, hydrogen gas generated during the incubation of the photosynthetic bacterium can be stored in a tank so as to be used as a fuel.

Next, the bacterial solution which had been incubated to an optimum level in the sealed and illuminated growth tank, was converted into the concentrated biomass by gathering the bacteria by means of a continuous centrifugal separator. Thereafter, the concentrated biomass was freeze-dried so as to obtain a dehydrated biomass. In the above process, when the incubated bacterial solution is transferred into the continuous centrifugal separator, it is possible to continuously obtain the identical photosynthetic bacterium, when, for example, 20% of the whole solution is always left in the growth tank so that the liquid medium prepared in the mixing tank for nutrition is added to the 20% of the liquid medium.

Note that, the reason why the sealed and illuminated growth tank was used in this method was because the photosynthetic bacterium grows optimally in the anaerobic atmosphere and under the illuminated condition (between 3000 lux and 10000 lux). Moreover, a stirring apparatus for stirring the liquid medium may be provided in the sealed and illuminated growth tank. The provision of the stirring apparatus can improve growth speed of the bacteria.

EXAMPLE

Described below is an example of the incubation of the photosynthetic bacterium. To begin with, in the mixing tank for nutrition, added into water of $1 \times 10^3$ cm$^3$ were:

| | |
|---|---|
| $(NH_4)_2SO_4$ | 0.3 g |
| $KH_2PO_4$ | 0.5 g |
| $MgSO_4 \cdot 7H_2O$ | 0.2 g |
| NaCl | 0.5 g |
| $NaHCO_3$ | 0.2 g |
| Yeast Extract | 0.01 g |

The respective above-listed nutrition were mixed into the water to prepare the base medium. Further, acetic acid 0.4 weight %, in the form of Na salt, and sucrose 5 weight % were added into the base medium, which was further adjusted to pH 7.0, for example, to prepare the liquid medium. Then, the liquid medium was transferred into the sealed and illuminated growth tank.

The growth tank, made of a transparent material, such as glass, in a cylinder-like shape, was illuminated by fluorescent lamps arranged in periphery of the growth tank at regular interval so as to illuminate evenly an inside of the growth tank. Meanwhile, the growth tank was provided with a stirring device that has blades of a size of a radius of the growth tank, in the growth tank. Therefore, the growth tank was capable of incubating the photosynthetic bacterium in a large quantity and with ease in the anaerobic atmosphere.

Next, a solution (bacterial concentration $10^6$ cell/cm$^3$) of *Rhodopseudomonus capsulatas* FERMBP-7434 strain was inoculated in a 20% ratio (v/v) over the total of the solution in the growth tank, then, a small quantity of a lactic acid bacterium (Lactobacillus bulgalicus, bacterial concentration $10^6$ cell/cm$^3$) was inoculated. The liquid medium was stirred at a rotation speed 13 times per minute at an incubation temperature 30° C. under illumination of 10000 lux. After 8 hours, the growth of the photosynthetic bacterium attained its optimum (stationary phase). Here, the liquid medium in the growth tank, a large quantity of the viscous material had been produced, while the photosynthetic bacterium was grown.

This liquid medium was transferred into a continuous centrifugal separator (sharp less type) so as to gather and concentrate the bacteria. The concentrated biomass was subjected to the freeze-drying, so that the biomass was obtained. The thus obtained biomass could be inoculated and obtained in a ratio of about 5 g per $1 \times 10^3$ of the liquid medium. As discussed later, the thus obtained biomass was quite active.

In the following, explained is a process of the freeze-drying. To begin with, the thus obtained concentrated biomass (about $10^{11}$ cell/cm$^3$) was frozen to store in a freezer, once. At the time of the freeze-drying, for example, $4 \times 10^3$ cm$^3$ was naturally thawed (about 12 hours), then poured and divided into 9 sucking bottles for $1.2 \times 10^3$ cm$^3$, approximately evenly (about 440 cm$^3$ each bottle).

Consequently, in a preliminary freezing tank (−45° C.), which had been filled in advance with an anti-freezing solution such as methanol, a bottom of the sucking bottles was touched with the anti-freezing solution by means of a prefreezer, while the sucking bottles were rotated, so that the concentrated biomass in the sucking bottle was frozen again so as to form a thin film along an inner wall of the sucking bottle (it was arranged that a thickness of the frozen biomass in the sucking bottle was about 8 mm, and the freezing time was about 20 minutes). The frozen concentrated biomass was stored in the freezer until the freezing of all the 9 bottles were completed.

After that, an inside of a trap of a freeze-drier was cooled down (−45° C.). After one hour since then (that is, when the cooling in the trap was completed), a vacuum pump was operated. After it was confirmed that a vacuum gauge of the vacuum pump was lowered below 26 Pa, preferably 4 to 6 Pa, the respective sucking bottles were connected with the trap. Consequently, the respective sucking bottles and the vacuum pump were linked via the trap. Then, the drying of the frozen biomass inside the respective sucking bottles was started at a room temperature (20° C. to 30° C.). The drying time, while the drying time depends on the room temperature, was about 40 hours. Note that, even though the above example used the freeze-dying method as the drying method of the concentrated biomass, it was also possible to use spray-drying as another drying method.

The thus obtained dried biomass was milled, for example, by using a crushing apparatus of a propeller-type (sample mill), where the rotation of the propellers was about 15000 rpm, so as to powder the dried biomass. Other powdering methods were, for example, a jet mill method or a ball mill method.

The powdered dried biomass may be used as the drug as it stands. Alternatively, the powdered dried biomass may be processed into a form of a tablet for a sake of easy ingestion. For example, a tablet-making machine of a high speed rotation type may be used for making the tablet. At the time of the tablet making process, it is possible to make the tablet without using an excipient, such as lactose, a binder, and a releasing agent such as magnesium stearate. Note that, if necessary, it may be possible to use an excipient for adjusting a dose.

In the above, explained was the example where *Rhodopseudomonas capsulatas* FERMBP-7434 strain was used. However, it may be possible to use other photosynthetic bacteria, such as *Chromatium vinosum* in a Thiorhodaceae family, or *Rhodospirillum Rubrum* in an Athiorhodaceae family.

Each quantification method for bacteriochlorophyll and a carotenoid material in dried biomass that is contained in the drug were carried out, based on "photosynthetic researching method" (by Sakae Kato, Kyoritsu Publishing Company: 1981).

Described below is the qualification method for the bacteriochlorophyll. To begin with, about 10 mg of a sample, which is the dried biomass, was taken and measured, and suspended in a physiological saline solution, 100 mm$^3$ (µl). Further, 4.9 cm$^3$ of acetone: methanol [7:2 (v/v)] was added. Then, the bacteriochlorophyll was extracted. Then, the extract was appropriately diluted. Absorbancy of the diluted solution at 770 nm was measured. A concentration of the bacteriochlorophyll was calculated out by the following equation (1):

$$\text{Bacteriochlorophyll}(\mu g/cm^3) = 12.15 \, A_{770} \quad (1)$$

In the following, 5 lots of samples 1. through 5. of the bacteriochlorophyll of dried biomass of the present drug, which was manufactured by the above method, were quantified, respectively. A result of the quantification is presented in Table 2.

TABLE 2

| SAMPLE NO. | SAMPLE WEIGHT (mg) | $A_{770}$ | CONTENT (mg/g) |
|---|---|---|---|
| 1. | 11.3 | 2.52 | 13.5 |
| 2. | 10.4 | 2.05 | 12.0 |
| 3. | 9.9 | 2.10 | 12.9 |
| 4. | 10.6 | 2.58 | 14.8 |
| 5. | 10.3 | 1.48 | 8.7 |

Note that, the absorbancy (770 nm) indicated by $A_{770}$ in Table 2 is a conversion value to an extracted undiluted solution (5 cm$^3$). The result showed that the contents (weight %) of the bacteriochlorophyll in the dried biomass of the drug were between 0.2 and 3.0, preferably, between 0.6 and 1.9.

In addition, because the measurement of the absorbancy was carried out at 770 nm (red region) in the quantification of the bacteriochlorophyll, it was noted that the measurement result of the bacteriochlorophyll was not affected at all, even if the carotinoid materials were contained in the diluted solution.

Next, the quantification method of the carotinoid materials is explained. To begin with, about 10 mg of a sample of the dried biomass was taken and measured, and was suspended in methanol, boiled to extract for one minute, and cooled down by ice. A supernatant was recovered by means of centrifugal separation. A precipitate was again suspended in the methanol. The extraction was repeated until a colorless extract was obtained, for example, for three times.

Ether in an equal quantity, and water in a double quantity with respect to the methanol extract were added into the methanol extract, and ether extraction was carried out. Then, an ether solution, which was separated out, was dehydrated. The thus obtained ether solution was measured to make 6 cm$^3$ of the ether solution. Then, absorption spectrum of the ether solution was measured.

An absorption maximum wavelength within a range from 400 to 550 nm of the absorption spectrum was determined, and absorbancy at the absorption maximum wavelength was measured. Using the absorbancy, the contents of the carotinoid materials were calculated out by the following equation (2):

$$c = D \cdot v/1.4 \times 10^5 \quad (2)$$

c: content of carotinoid material (mol),
D: absorbancy at the absorption maximum wavelength,
v: volume of ether solution (10$^3$ cm$^3$, that is, one liter),
1.4×10$^5$: an average molecular absorption coefficient of carotinoid material.

Because the maximum absorption of the carotinoid materials exists within the range from 400 to 550 nm, the absorption maximum wavelength within the range was measured from the absorption spectrum (see FIG. 1) of the ether solution. The carotinoid materials were quantified, based on the absorbancy at the absorption maximum wavelength.

Shown below in Table 3, are each quantification result of the carotinoid material as to the respective samples 1. to 5. discussed above. Moreover, absorption spectrum of the sample 1. is illustrated in FIG. 1. Absorption spectrums of the other samples 2. to 5. also showed a same pattern.

TABLE 3

| SAMPLE No. | SAMPLE WEIGHT (mg) | A.M.W (nm) | Absorbancy | CONTENT (µmol/g) |
|---|---|---|---|---|
| 1. | 9.4 | 476.5 | 0.756 | 3.45 |
| 2. | 10.8 | 476.0 | 0.868 | 3.44 |
| 3. | 11.4 | 476.0 | 0.782 | 2.94 |
| 4. | 9.6 | 476.0 | 0.666 | 2.97 |
| 5. | 10.4 | 476.0 | 0.733 | 3.02 |

ABBREVIATION:
A.M.W stands for absorbancy maximum wavelength.

The result in Table 3 explains that contents (µmol/g) of the carotinoid material in the dried biomass of the drug were between 0.5 and 7.5, preferably between 2.4 and 4.0.

Moreover, according to the result in FIG. 1, since no absorbancy was measured above 600 nm in a visible region, it was found out that, at most, less than a quantity of a detection limit of the bacteriochlorophyll was contained in the ether extract. Therefore, as to the quantification method of the carotinoid materials, it was found out that the quantification of the carotinoid materials was not affected at all, even though the bacteriochlorophyll was contained in the drug.

Next, as to the respective samples 1. to 5. of the drug, and water-washed samples of the samples 1. to 5., were respectively subjected to acid hydrolysis, and then quantified in terms of the following respective neutral monosaccharides, by means of a high performance liquid chromatographic method. The quantification of the neutral monosaccharides is for specify the viscous material contained in the dried biomass of the drug of the present invention.

The quantification method is described below. To begin with, as to preparation of the water-washed samples, about 0.5 g of each sample was weighed and placed in a centrifugal tube. 25 cm$^3$ of water was added into the centrifugal tube and stirred, then, was subjected to ultrasonic extraction for 3 minutes, then was subjected to centrifugal separation (12,000 rpm, 5 minutes) so as to remove a supernatant. 25 cm$^3$ of water was added into a residue in the centrifugal tube and the water-washing process was processed again for two times in the same manner.

The residue, to which 25 cm$^3$ of acetone was added in order to remove water, was stirred, then was subjected to centrifugal separation (12,000 rpm, 5 minutes) so as to remove a supernatant. After acetone remained in the centrifugal tube was volatilized under a nitrogen stream, the residue was air-dried to be the water-washed sample.

Next, explained is preparation of a test solution. To begin with, after 0.3 g to 0.6 g of each sample or 0.3 g to 0.6 g of each water-washed sample were weighed, 4 cm$^3$ of 72% sulfuric acid was added to the samples and the water-washed samples. Then, the samples were stirred for one hour at a room temperature (the water-washed samples were stirred for two hours).

Then, the samples and the water-washed samples were diluted with 112 cm$^3$ of water (sulfuric acid concentration: 4%), and were subjected to hydrolysis for one hour in an autoclave (121° C.). After the samples and the water-washed samples were cooled down to the room temperature, and neutralized by a sodium hydroxide solution of 30 w/v %, their volumes were adjusted to 200 cm$^3$ with water. Then, the samples and water-washed samples were filtered (No. 5B, supplied from Advantech Toyo Co., Ltd.), and further filtered with a membrane filter having a pore diameter of 0.45 μm, thereby obtaining a filtrate as the test solution.

The contents of monosaccharides (glucose, ribose, rhamnose, and fucose) were measured by the liquid chromatographic method. A result of the measurement is shown in Table 4. The measurement result indicates the contents (g) per 100 g of the dried biomass of the drug.

TABLE 4

|  | 1 | 2 | 3 | 4 | 5 |
|---|---|---|---|---|---|
| GLUCOSE | | | | | |
| BEFORE WASHING | 5.1 | 4.6 | 4.8 | 5.0 | 5.1 |
| AFTER WASHING | 2.1 | 2.2 | 2.2 | 2.2 | 1.7 |
| RIBOSE | | | | | |
| BEFORE WASHING | 0.7 | 0.7 | 0.7 | 0.7 | 0.7 |
| AFTER WASHING | 0.5 | 0.6 | 0.5 | 0.6 | 0.6 |
| RHAMNOSE | | | | | |
| BEFORE WASHING | 2.0 | 2.0 | 2.0 | 2.0 | 2.2 |
| AFTER WASHING | 0.9 | 0.8 | 0.8 | 0.9 | 1.0 |

TABLE 4-continued

|  | 1 | 2 | 3 | 4 | 5 |
|---|---|---|---|---|---|
| FUCOSE | | | | | |
| BEFORE WASHING | 1.2 | 1.2 | 1.2 | 1.2 | 1.7 |
| AFTER WASHING | 0.2 | ND | ND | ND | 0.3 |

In Table 4, ND indicates that the content was less than the detection limit (0.2 g/100 g).

According to the result in Table 4, it was found out that, in the acid hydrolyzed samples of the dried biomass of the drug before washing, the contents (weight %) of glucose were in a range between 2.4 and 7.5, more preferably between 3.5 and 6.5, the contents (weight %) of ribose were in a range between 0.3 and 1.1, more preferably between 0.4 and 1.0, the contents (weight %) of rhamnose were in a range between 1.0 and 3.3, more preferably between 1.2 and 3.0, the contents (weight %) of fucose were in a range between 0.6 and 2.6, more preferably 0.8 and 2.4.

Moreover, according to the result in Table 4, it was found out that, in the acid hydrolyzed sample of the dried biomass of the drug after washing, the contents (weight %) of glucose were in a range between 0.8 and 3.3, more preferably between 1.0 and 3.0, the contents (weight %) of ribose were in a range between 0.2 and 1.0, more preferably between 0.3 and 0.9, the contents (weight %) of rhamnose were in a range between 0.4 and 2.0, more preferably between 0.5 and 1.6, the contents (weight %) of fucose were less than 0.6, more preferably less than 0.5.

Next, as to the dried biomass of the drug of the present invention, an acute oral toxicity test (limit test) was carried out. In short, the acute oral toxicity test (limit test) as to samples of the drug was carried out by using mice, in accordance with OECD (Organization for Economic Cooperation and Development) chemical substance test guide (1987).

A test group of male and female mice was subjected to single-time oral administration of 2,000 mg/kg of the sample, while a control group of them was orally given purified water, as a control solvent, one time. As a result, no abnormality or expiry of the tested animals was observed. Therefore, it was judged that an LD50 value of the single-time oral administration as to the tested mice was more than or equal to 2,000 mg/kg for both the male and the female mice.

The test is explained below. To begin with, the sample of the dried biomass of drug was suspended in purified water to prepare 100 mg/cm$^3$ of a test solution.

The tested animal was as follows. To being with, ICR-type male and female mice of 4 week old were purchased from Japan SLC Co., Ltd. After the mice were preliminarily kept for about one week for checking their general condition was not abnormal, the mice were used for the test. The tested animals were put in cages made of polycarbonate, which respectively contained 5 of the tested animals, and were kept in a breeding room in which a room temperature was set at 23±2° C. and illumination time was set at 12 hours per day. Feed (solid feed for mice and rats; lab MR stock, made by Japan agricultural products industry Co., Ltd.) and drinking water (tap water) were freely given.

The testing method was as follows. To begin with, both the tested group and the control group had 10 of the male and the female mice, respectively. Before the administration, the tested animals were fasted for about 4 hours. After their body weight was measured, the tested group, both the males and the females, was subjected to a forcible single-time oral administration of the test solution whose dosage, a sample administration amount, was 2,000 mg/kg, by using a stomach sonde. As to the control group, 0.6 cm³ of the purified water was administered to the males, and 0.5 cm³ of the purified water was administered to the females, in the same manner.

The observation period was 14 days. Observation was carried out frequently on the day of the administration. The observation was carried out once a day from the following day. On 7 days and 14 days since the administration, the body weight was measured, and a comparison between the groups was carried out by t-inspection with a 5% level of significance. At an end of the observation period, all the tested animals were anatomized. A result of the test was as shown in Table 5. In parentheses in Table 5, shown is a number of the animals.

TABLE 5

| ADMINISTRATED | | AFTER AD. (DAY) | |
|---|---|---|---|
| GROUPS | BEFORE AD. | 7 | 14 |
| MALE TESTED G. | 28.2 ± 0.8 (10) | 33.9 ± 1.3 (10) | 37.7 ± 2.0 (10) |
| CONTROL G. | 28.1 ± 0.8 (10) | 33.8 ± 0.8 (10) | 36.8 ± 1.8 (10) |
| FEMALE TESTED G. | 24.3 ± 0.6 (10) | 27.0 ± 1.2 (10) | 28.9 ± 1.4 (10) |
| CONTROL G. | 24.0 ± 0.5 (10) | 27.4 ± 1.6 (10) | 29.3 ± 1.9 (10) |

ABBREVIATION:
AD. STANDS FOR ADMINISTRATION.
G. STANDS FOR GROUP.

In the above test, no expiry was observed for both the males and the females during the observation period. No abnormality was observed for both the males and the females during the observation period. As to the body weight measurement on 7 days and 14 days since the administration, no difference between the groups in terms of weight gain was observed as for both the males and the females, as shown in Table 4. In the anatomy after the observation period, no abnormality was found in main internal organs of all the tested animals for both the males and the females.

According to the OECD chemical substance test guide (1987), it is instructed that an intensive test for determining an LD50 value is necessary in case expiry is observed with dosage of 2000 mg/kg.

However, in the above test result, no expiry was observed with this dosage, and no abnormality was found at the anatomy, too. Therefore, it was judged that the LD50 value of the single-time oral administration to the tested mice was more than or equal to 2000 mg/kg for both the males and the females.

Because of this, it was proved that the drug of the present invention does not adversely affect a human body even in case of regular intake of the drug.

In the following, morphological characteristics, growth conditions, and physiological characteristics of *Rhodopseudomonas capsulatas* are described.

a. Morphological Characteristics

*Rhodopseudomonas capsulatas* has a flagellum and is quite motile. Generally, they are short bacilli (width 0.5μ× length 1.0μ), while some are long bacilli (width 0.5μ to 0.7μ×length 6.0μ), depending on a type of liquid media and incubation periods. In other words, they shows polymorphism.

b. Growth Conditions
The growth result (anaerobic and under illumination) on various media are described below.

| Meat Extract | + | Lactic Acid | ++ |
|---|---|---|---|
| Peptone Water | +++ | Succinic Acid | + |
| Potato Medium | − | Malic Acid | + |
| Thiosuifate | − | Butyric Acid | ++ |
| Alanine | + | Crotonic Acid | + |
| Leucine | − | Pyruvic Acid | ++ |
| Asparagine | + | Ethanol | + |
| Aspartic Acid | − | Mannitol | − |
| Glutamic Acid | + | Sorbitol | − |
| Tartaric Acid | − | Mannose | − |
| Citric Acid | − | Fructose | − |
| Glutaric Acid | + | Glycerol | − |
| Acetic Acid | + | | |
| Propionic Acid | +++ | | |

(All the substrates were used in 0.2 weight % concentration.)
Note:
+++ Growth was good.
+ Growth was possible.
− Growth was impossible.

c. Physiological Characteristics
1) Optimal Growth Condition
pH 7.2, temperature 27° C.,
anaerobic illumination 10,000 lux
2) Condition which allows the growth
pH 6.0 to pH 8.5, temperature 23° C. to 39° C., aerobic to anaerobic dark condition to illumination condition
3) Gram Staining Characteristics
Negative
4) Anti-acid Characteristics
Positive
5) Indole Production
Negative
6) Hydrogen Sulfide Production
Negative
7) Ability for Nitrogen Gas Fixation
Positive
8) It also carries out denitrification in a nitrate medium, in which nitric acid is reduced and converted to a gas of $N_2$, on contrary to the nitrogen fixation.
9) Catalase Production
Positive
10) Gelatine Liquefaction
Negative
11) Starch Hydrolysis
Negative
12) Ability to oxidize Methylene Blue of a reduction type, Methyl (or Benzyl) Biorodien pigment of a reduction type
Positive
13) It requires Biotin, Thiamin, and Nicotinic Acid as growth factors.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

What is claimed is:
1. A drug, containing:
biomass prepared by incubating *Rhodopseudomonas capsulatas* FERMBP-7434 strain together with a lactic acid bacterium to produce a biomass comprising a viscous material; wherein after being subjected to water-washing and subsequently to acid hydrolysis, the biomass has a glucose content ranging from 0.8 to 3.3 weight %, a ribose content ranging from 0.2 to 1.0 weight %, a rhamnose content ranging from 0.4 to 2.0 weight %, and a fucose content of 0.6 weight % or less.

2. The drug as set forth in claim 1, wherein:
the biomass contains bacteriochlorophyll in a range of from 0.2 to 3.0 weight %.

3. The drug as set forth in claim 1, wherein:
the biomass contains bacteriochlorophyll in a range of from 0.6 to 1.9 weight %.

4. The drug as set forth in claim 1, wherein:
the biomass contains a carotinoid material in a range of 0.5 to 7.5 µmol/g.

5. The drug as set forth in claim 1, wherein:
the biomass contains a carotinoid material in a range of 2.4 to 4.0 µmol/g.

6. The drug as set forth in claim 1, wherein:
after being subjected to acid hydrolysis, the biomass has a glucose contents ranging from 2.4 to 7.5 weight %, a ribose content ranging from 0.3 to 1.1 weight %, a rhamnose content ranging from 1.0 to 3.3 weight %, and a fucose content ranging from 0.6 to 2.6 weight %.

7. The drug as set forth in claim 1, wherein:
after subjected to acid hydrolysis, the biomass has a glucose content ranging from 3.5 to 6.5 weight %, a ribose content ranging from 0.4 to 1.0 weight %, a rhamnose content ranging from 1.2 to 3.0 weight %, and a fucose content ranging from 0.8 to 2.4 weight %.

8. The drug as set forth in claim 1, wherein:
after being subjected to water-washing and subsequently to acid hydrolysis, the biomass has a glucose content ranging from 1.0 3.0 weight %, a ribose content ranging from 0.3 to 0.9 weight %, a rhamnose content ranging from 0.5 to 1.6 weight %, and a fucose content of 0.5 weight % or less.

9. The drug as set forth in claim 1, wherein:
the lactic acid bacterium is *Lactobacillus* spp.

10. The drug as set forth in claim 1, wherein:
the lactic acid bacterium is *Lactobacillus bulcialicus*.

11. A method of manufacturing a drug, comprising the steps of:
incubating in a liquid medium *Rhodopseudomonas capsulatas* FERMBP-7434 strain together with a lactic acid bacterium to produce a biomass comprising a viscous material in the liquid medium, and
separating the biomass comprising a viscous material from the liquid medium.

\* \* \* \* \*